United States Patent
Hedl et al.

(10) Patent No.: US 8,831,895 B2
(45) Date of Patent: Sep. 9, 2014

(54) STRUCTURAL DAMAGE INDEX MAPPING SYSTEM AND METHOD

(75) Inventors: Radek Hedl, okres Blansko (CZ); Jindrich Finda, Brno (CZ); Karel Adamek, Brno (CZ)

(73) Assignee: Honeywell International Inc., Morristown, NJ (US)

( * ) Notice: Subject to any disclaimer, the term of this patent is extended or adjusted under 35 U.S.C. 154(b) by 645 days.

(21) Appl. No.: 13/169,858

(22) Filed: Jun. 27, 2011

(65) Prior Publication Data

US 2012/0330570 A1    Dec. 27, 2012

(51) Int. Cl.
G06F 19/00 (2011.01)
G01N 29/06 (2006.01)
G01N 29/07 (2006.01)
G01N 29/04 (2006.01)
G01N 29/44 (2006.01)

(52) U.S. Cl.
CPC ...... *G01N 29/043* (2013.01); *G01N 2291/0258* (2013.01); *G01N 29/069* (2013.01); *G01N 29/07* (2013.01); *G01N 29/4427* (2013.01); *G01N 2291/105* (2013.01)
USPC ................ 702/39; 702/34; 702/35; 73/587; 73/594

(58) Field of Classification Search
USPC ........... 702/39, 184, 34, 29, 109; 73/587, 594
See application file for complete search history.

(56) References Cited

U.S. PATENT DOCUMENTS

| | | | |
|---|---|---|---|
| 5,195,046 A | 3/1993 | Gerardi et al. | |
| 5,293,555 A | 3/1994 | Anthony | |
| 5,774,376 A | 6/1998 | Manning | |
| 5,841,031 A | 11/1998 | Chung | |
| 5,911,158 A | 6/1999 | Henderson et al. | |
| 6,006,163 A | 12/1999 | Lichtenwalner et al. | |
| 6,370,964 B1* | 4/2002 | Chang et al. | 73/862.046 |
| 7,103,507 B2* | 9/2006 | Gorinevsky et al. | 702/184 |
| 7,426,447 B2 | 9/2008 | Pado | |
| 7,458,266 B2 | 12/2008 | Beard et al. | |
| 7,536,912 B2 | 5/2009 | Kim | |
| 7,647,206 B2 | 1/2010 | Ford | |
| 7,668,665 B2 | 2/2010 | Kim | |
| 7,672,793 B2 | 3/2010 | Beard | |
| 7,822,258 B2 | 10/2010 | Senibi et al. | |
| 2006/0032313 A1 | 2/2006 | Austin et al. | |
| 2006/0179949 A1 | 8/2006 | Kim | |
| 2007/0018083 A1 | 1/2007 | Kumar et al. | |
| 2007/0095138 A1 | 5/2007 | El-Bakry et al. | |
| 2009/0055106 A1 | 2/2009 | Finkel et al. | |

* cited by examiner

*Primary Examiner* — Jonathan C Teixeira Moffat
*Assistant Examiner* — Hien Vo
(74) *Attorney, Agent, or Firm* — Ingrassia Fisher & Lorenz, P.C.

(57) ABSTRACT

A system and method for detecting and evaluating structural defects are provided. Baseline data representative of sensed ultrasonic waves that were transmitting into a structure with no defects are stored. Ultrasonic waves are transmitted into the structure from a plurality of actuators that are coupled to the structure. The ultrasonic waves that are transmitted into the structure from the plurality of actuators are sensed, with a plurality of sensors that are coupled to the structure and spaced apart from the actuators, to thereby generate and supply sensor data. Signal difference coefficients are calculated from the baseline data and the sensor data. The calculated signal difference coefficients are spatially mapped to detect one or more structural defects in the structure.

21 Claims, 10 Drawing Sheets

| PATHS (ACTUATOR-SENSOR) | MEASUREMENT NO. (FAILURE STATES) | | | | |
|---|---|---|---|---|---|
| | 1 | ... | N-1 | N |
| 1 | DI$_{1,1}$ | ... | DI$_{N-1,1}$ | DI$_{N,1}$ |
| 2 | DI$_{1,2}$ | ... | DI$_{N-1,2}$ | DI$_{N,2}$ |
| ... | ... | ... | ... | ... |
| K-1 | DI$_{1,K-1}$ | ... | DI$_{N-1,K-1}$ | DI$_{N,K-1}$ |
| K | DI$_{1,K}$ | ... | DI$_{N-1,K}$ | DI$_{N,K}$ |

FIG. 14

STRUCTURAL DAMAGE INDEX MAPPING SYSTEM AND METHOD

TECHNICAL FIELD

The present invention generally relates to structural health monitoring, and more particularly relates to a system and method for detecting, localizing, and evaluating the size of structural defects.

BACKGROUND

Structural health monitoring is becoming of ever-increasing significance for many industries. One industry for which this is becoming especially significant is the aerospace industry. This is because, among other things, the structural integrity of systems and components in the aerospace industry can possibly cause in-flight shutdowns, take-off aborts, delays, or cancellations, all of which can result in significant industry and consumer costs.

Some presently known structural health monitoring systems use arrays of various sensors. The use of such arrays, which can range from tens to hundreds of sensors, exhibits certain drawbacks. For example, installing each of the sensors one-by-one can be both labor-intensive and time-consuming. When the sensors are implemented as phase arrays, which can be very sensitive to inaccuracies in the sensor placement, it may be necessary to assure the precise position of each of the sensors. Moreover, the sensor wiring can be relatively complicated, and the length, volume, and weight of the sensor wiring can be significant.

In addition to the above, various numerical methods have been developed to provide visual representations of damage maps for structural defect detection, localization, and sizing. Included among these known numerical methods are various computer tomography (CT) methods. The presently known CT methods can provide relatively precise defect images, but can also be relatively time-consuming and computationally intensive. Moreover, many CT methods rely on high density coverage of the monitored area. As a result, the CT methods may not be useful when real-time structural health monitoring is desired, because sparse sensor arrays are generally used for such applications.

Various numerical methods do exist for use with sparse sensor arrays. These methods are typically based on the detection of waves scattered by a defect, the use of a geometrical approach to spatial mapping of the scatters. For relatively complex structures, indentifying a wave reflected by a defect can be extremely challenging due to the presence of various structural elements such as stringers, stiffeners, borders, holes, rivets, bolts, etc., which can be sources of background reflections. One numerical method that has been developed that does not suffer from this drawback is known as the RAPID (Reconstruction Algorithm for Probabilistic Inspection of Defects) algorithm. The RAPID algorithm is based on the evaluation of signal differences, using a correlation analysis, between a baseline signal and actual signals in the direct path between sensor/actuator pairs. However, the RAPID algorithm exhibits several drawbacks of its own. For example, it is sensitive to phase synchronization between the baseline and actual signals. Moreover, images that are generated based on the RAPID algorithm can include false artifacts if certain parameters are not set optimally. These false artifacts may also be generated due to the non-uniform coverage provided by the network of direct paths between sensor/actuator pairs.

Hence, there is a need for a system and method for detecting, localizing, and evaluating the size of structural defects in real-time that does not exhibit the drawbacks noted above. Namely, a system and method that does not rely on the precise positioning of individual sensors and/or relatively complicated, long, voluminous, and heavy sensor wiring and/or is relatively insensitive to phase synchronization between the baseline and actual signals and/or does not generate images that include false artifacts if certain parameters are not set optimally. The present invention addresses one or more of these needs.

BRIEF SUMMARY

In one embodiment, a method for detecting and evaluating structural defects includes storing baseline data associated with a structure. The baseline data representative of sensed ultrasonic waves that were transmitting into the structure with no defects. Ultrasonic waves are transmitted into the structure from a plurality of actuators that are coupled to the structure. The ultrasonic waves that are transmitted into the structure from the plurality of actuators are sensed, with a plurality of sensors that are coupled to the structure and spaced apart from the actuators, to thereby generate and supply sensor data. Signal difference coefficients are calculated from the baseline data and the sensor data. The calculated signal difference coefficients are spatially mapped to detect one or more structural defects in the structure.

In another embodiment, a structural defect detection and evaluation system includes a plurality of first sensor/actuators, a plurality of second sensor/actuators, and a processor. The first sensor/actuators are each adapted to be coupled to a structure, and are each configured to selectively transmit ultrasonic waves into the structure. The second sensor/actuators are each adapted to be coupled to the structure and, when coupled thereto, to be spaced apart from each of the first sensor/actuators. Each second sensor/actuator is configured to selectively sense the ultrasonic waves transmitted from one or more of the first sensor/actuators and generate sensor data. The processor is coupled to receive the sensor data and is configured, upon receipt thereof, to calculate signal difference coefficients from the sensor data and baseline data, the baseline data representative of sensed ultrasonic waves that were transmitting into the structure with no defect present, and spatially map the calculated signal difference coefficients to detect one or more structural defects in the structure.

In yet another embodiment, a structural defect detection and evaluation system includes a plurality of first sensor/actuators, a plurality of second sensor/actuators, a display device, and a processor. Each of the first sensor/actuators is mounted on a first flexible printed circuit and is adapted to be coupled to a structure. Each first sensor/actuator is additionally configured to selectively transmit ultrasonic waves into the structure. Each of the second sensor/actuators is mounted on a second flexible printed circuit and is adapted to be coupled to the structure. Each second sensor/actuator, when coupled to the structure, is spaced apart from each of the first sensor/actuators, and each is configured to selectively sense the ultrasonic waves transmitted from one or more of the first sensor/actuators and generate sensor data. The display device is coupled to receive image rendering display commands and is configured, upon receipt thereof, to selectively render images representative of the image rendering display commands. The processor is coupled to receive the sensor data and is configured, upon receipt thereof, to calculate signal difference coefficients from the sensor data and baseline data, the baseline data representative of sensed ultrasonic waves that were transmitting into the structure with no defect present, spatially map the calculated signal difference coefficients to detect one or more structural defects in the structure, generate a damage map from the spatially mapped signal difference coefficients, and selectively generate image rendering display commands representative of the damage map.

Furthermore, other desirable features and characteristics of the structural damage index mapping system and method will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein:

FIG. 14 depicts an input matrix that may be used with the PCA process depicted in FIG. 13.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
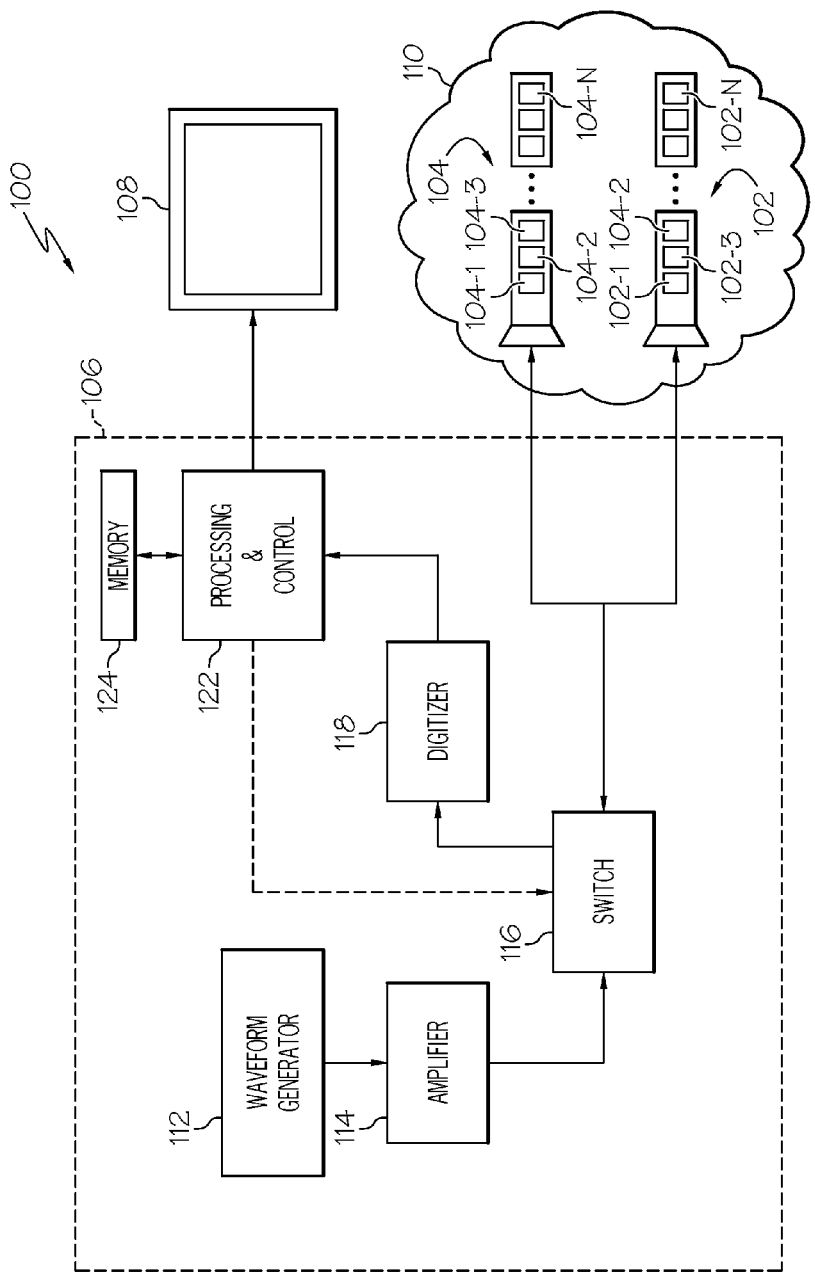
FIG. 1 depicts a functional block diagram of an exemplary embodiment of a structural defect detection and evaluation system.

Referring first to FIG. 1, a functional block diagram of one embodiment of a structural defect detection and evaluation system is depicted. The depicted system 100 includes a plurality of first sensor/actuators 102 (102-1, 102-2, 102-3 . . . , 102-N), a plurality of second sensor/actuators 104 (104-1, 104-2, 104-3 . . . , 104-N), a processor 106, and a display device 108. The first sensor/actuators 102 and the second sensor/actuators 104 are adapted to be coupled to a structure 110. As FIG. 1 further depicts, when the first and second sensor/actuators 102, 104 are indeed coupled to the structure 110, each of the plurality of first sensor/actuators 102 are preferably spaced apart from each of the plurality of second sensor/actuators 104. The first and second sensor/actuators 102, 104 are each configured to selectively transmit ultrasonic waves into the structure 110. The first and second sensor/actuators 102, 104 are additionally configured to selectively sense the ultrasonic waves transmitted from one or more of the first or second sensor/actuators 102, 104, and generate sensor data representative thereof. In the depicted embodiment, the first and second sensor/actuators 102, 104 are configured to transmit and sense ultrasonic Lamb waves. It will be appreciated, however, that this is merely exemplary of one particular embodiment, and that other types of ultrasonic waves may be used.

Figure 2:
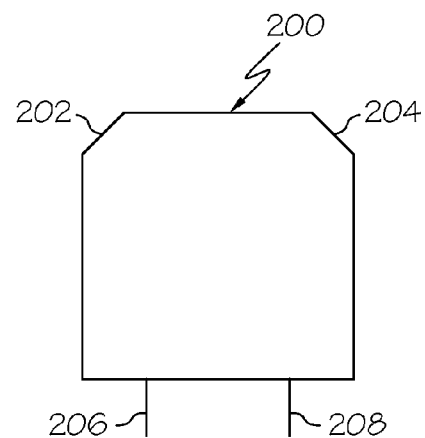
FIG. 2 depicts an embodiment of a shear piezoelectric sensor/actuator that may be used to implement the system of FIG. 1.

The first and second sensor/actuators 102, 104 may be variously configured and implemented to provide the above-described functions. In one embodiment, which will now be described in more detail, the first and second sensor/actuators 102, 104 are each implemented using a shear piezoelectric sensor/actuator. It will be appreciated, however, that various other types of actuators that exhibit a normal displacement to the surface of a structure 110 may also be used. Referring now to FIG. 2, one exemplary embodiment of a shear piezoelectric sensor/actuator 200 is depicted. The depicted shear piezoelectric sensor/actuator 200 is a shear plate piezoelectric-ceramic sensor/actuator, and more particularly a shear plate lead-zironate-titanate (PZT) sensor/actuator. The particular shear plate sensor/actuator 200 that is depicted in FIG. 2 is manufactured by Noliac A/S of Denmark. For this particular type of shear plate sensor/actuator 200, the direction of operation is indicated by the chamfers 202, 204. More specifically, if a positive voltage supplied to either electrode 206, 208, this electrode 206, 208 will undergo a relative displacement toward the chamfered edge.

The depicted sensor/actuator 200 also generates symmetric (S-mode) Lamb waves better than it does asymmetric (A-mode) Lamb waves. It has been determined that S-mode Lamb waves provide better performance and sensitivity to the expected types of defects. Further, S-modes Lamb waves are less dispersive and have a higher propagation velocity than corresponding A-mode Lamb waves in the frequency band (e.g., 100-700 kHz) that is used, in at least one embodiment, for signal measurement.

Figure 3:
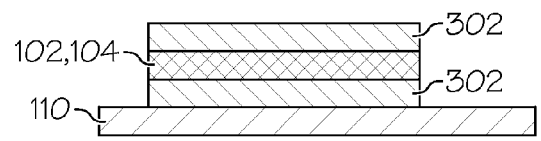
FIG. 3 is a simplified cross section view of the exemplary sensor/actuator of FIG. 2 coupled to a structure.

The first and second sensor/actuators 102, 104 may be individually coupled to the structure 110 or collectively coupled via common substrates. For either embodiment, the first and second sensor/actuators 102, 104 may be electrically insulated from the structure 100. This may be accomplished, as depicted in FIG. 3, by disposing a suitable electrical insulator 302, such as an inactive ceramic plates or a polyimide film insulator, between each sensor/actuator 102, 104 and the structure 110 and, if needed or desired, over each sensor/actuator 102, 104. As was noted above, individually coupling the sensor/actuators 102, 104 to the structure 110 can be labor-intensive and time-consuming Moreover, when the sensor/actuators 102, 104 are implemented in arrays, as in the embodiment depicted in FIG. 1, it may be necessary to assure the precise position of each of the sensor/actuators 102, 104, and the wiring for the sensor/actuators 102, 104 can be relatively complicated, and have significant length, volume, and weight. Hence, in one particular embodiment, the first sensor/actuators 102 are mounted on one common substrate, and the second sensor/actuators 104 are mounted on separate common substrate. These substrates are then coupled to the structure 110. The manner in which this is accomplished will now be described.

Figure 4:
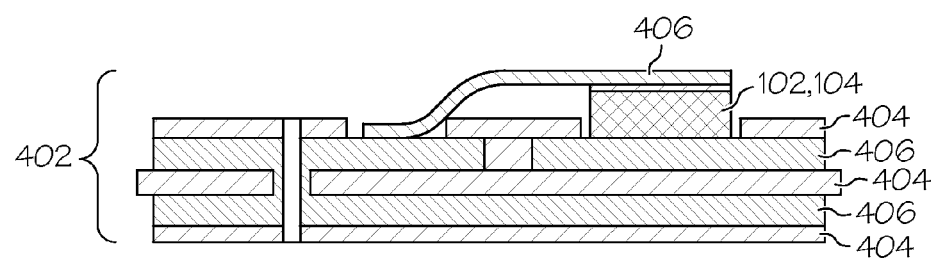
FIG. 4 depicts a simplified cross section view of a portion of a substrate showing the sensor/actuator of FIG. 2 mounted thereon.

Turning now to FIG. 4, a simplified cross section view of a portion of a substrate 402 showing a single sensor/actuator 102, 104 mounted thereon is depicted. Although the type of substrate may vary, in the depicted embodiment the substrate 402 is implemented using a flexible printed circuit (FPC) strip. The depicted FPC strip 402 includes layers of flexible plastic 404, such as such as polyimide, PEEK or transparent conductive polyester, and conductive foil 406, such as copper, circuit traces. The FPC strip 402 provides good mechanical contact between the structure 110 and each sensor/actuator 102, 104, relatively simple electrical connection to each sensor/actuator 102, 104, and is sufficiently robust for handling and installation. Though not depicted, a polyamide overlay or solder mask overlay may be provided to protect portions the FPC strip 402 from environmental attack. Each sensor/actuator 102, 104 may be additionally protected via a suitable coating, such as lacquer. Moreover, any conductive foil 406 that may be exposed to the surrounding environment may be plated with gold to provide additional corrosion protection and to improve electrical conductivity with conductive epoxy or solder, either of which may be used to electrically connect the sensor/actuators 102, 104 to the FPC strip 402. The FPC strip 402 may be electrically connected to external equipment, such as the processor 106 depicted in FIG. 1, via screened/shielded cables and/or various suitable connectors.

Figure 5:
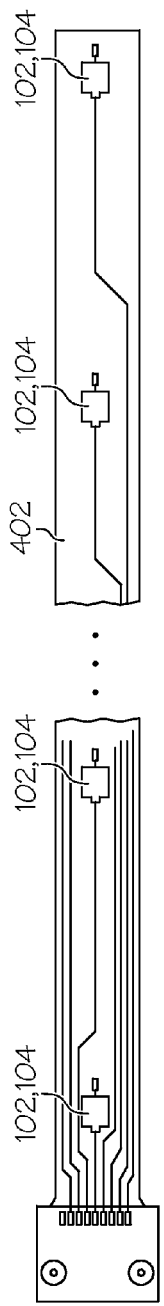
FIG. 5 depicts an embodiment of a flexible printed circuit with a plurality of sensor/actuators distributed thereon in a linear array.
Figure 6:
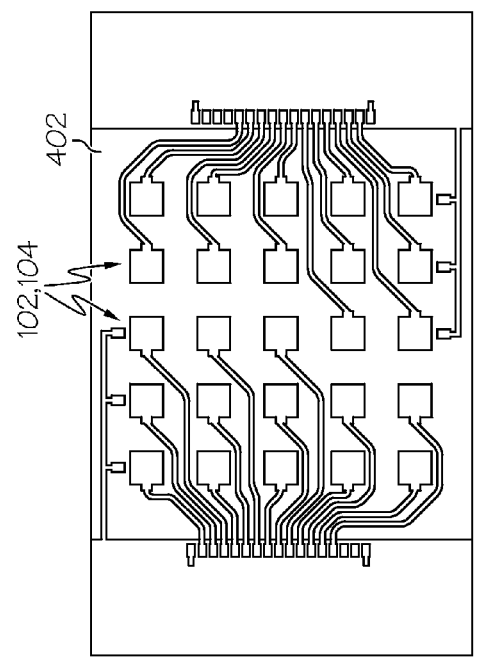
FIG. 6 depicts an embodiment of a flexible printed circuit with a plurality of sensor/actuators distributed thereon in a 5×5 matrix-type array.

The number sensor/actuators 102, 104 that may be disposed on each FPC strip 402 may vary. Furthermore, the layout of the sensor/actuators 102, 104 on each FPC strip 402 may vary. For example, a plurality of sensor/actuators 102, 104 may be distributed on each FPC strip 402 in a linear array or as an N×M matrix-type array. An exemplary embodiment in which a plurality of sensor/actuators 102, 104 are distributed on an FPC strip 402 in a linear array is depicted in FIG. 5, and another exemplary embodiment in which a plurality of sensor/actuators 102, 104 are distributed on an FPC strip 402 in a 5×5 matrix-type array is depicted in FIG. 6. It will be appreciated that the arrangement of the circuit traces in each of the depicted embodiments may vary depending, for example, on the type and/or size of sensor/actuator that is used, and that those depicted are merely exemplary. It will additionally be appreciated that the spacing between each sensor/actuator 102, 104 may vary. Moreover, a 5×5 matrix-type array is merely exemplary, and matrices of various other dimensions may be implemented.

Returning once again to FIG. 1, the processor 106 is coupled to receive the sensor data from the first and second sensor/actuators 102, 104, and is configured, upon receipt thereof, to detect whether one or more structural defects are present in the structure 110. The processor 106 is additionally configured to selectively excite, preferably one at a time, each of the first and second sensor/actuators 102, 104. For example, in the embodiment depicted in FIG. 1, the processor 106 will excite, one at a time, each of the first sensor/actuators 102, and receive the sensor data that each of the second sensor/actuators 104 generates in response to the ultrasonic waves that each of the first sensor/actuators 102 individually transmitted into the structure 110. The processor 106 will then excite, one at a time, each of the second sensor/actuators 104, and receive the sensor data that each of the first sensor/actuators 102 generates in response to the ultrasonic waves that each of the second sensor/actuators 104 individually transmitted into the structure 110.

The processor 106 may be variously configured and implemented to carry out each of the functions described above, and the additional functions that will be described below. In the depicted embodiment the processor 106 is configured to implement a waveform generator 112, an amplifier 114, a switch 116, an analog-to-digital (A/D) converter 118, and various processing and control functions 122. It may thus be appreciated that one or more of the waveform generator 112, amplifier 114, switch 116, A/D converter 118, and the various processing and control functions 122 may be implemented using separate signal processing circuits and/or devices. Alternatively, one or more of these functions may be implemented as part of a single processing device, such as a general purpose processor or microprocessor.

Regardless of how each of the above-mentioned functions is implemented, the waveform generator 112 is configured to generate an sensor/actuator excitation signal 113, which is supplied to the amplifier 114 for suitable amplification and filtration. The amplified and filtered excitation signal 115 is supplied to the switch 116, which is also coupled to the processing and control functions 122 and to each of the first and second sensor/actuators 102, 104. The switch 116, under control of the processing and control functions 122, selectively supplies the amplified and filtered excitation signal 115, one at a time, to each of the first or second sensor/actuators 102, 104. The switch additionally receives the analog sensor signals 117 from each of the first and sensor/actuators 102, 104, and supplies the analog sensor signals 117 to the A/D converter 118. The A/D converter 118 converts the analog sensor signals 117 to digital sensor data 119, which is supplied to the processing and control functions 122.

Figure 7:
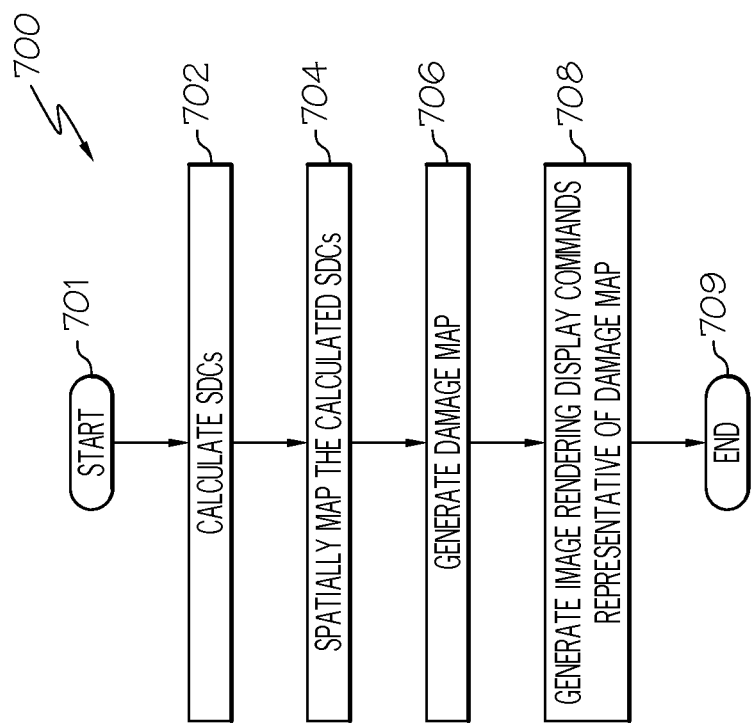
FIG. 7 depicts a process, in flowchart form, that is implemented by the system of FIG. 1 to detect whether one or more structural defects are present in a structure.

The processing and control functions 122, in addition to controlling the switch 116, process the sensor data 119 to detect whether one or more structural defects are present in the structure 110, and at least selectively supply image rendering display commands to the display device 118. To detect whether one or more structural defects are present in the structure 110, the processing and control functions 122 are configured to implement a process. This process 700, which is depicted in flowchart form in FIG. 7, will now be described. In so doing, it should be noted that the parenthetical references in the following description refer to like reference numerals in FIG. 7.

The process 700 includes the step of calculating signal difference coefficients (SDCs) from baseline data and from the sensor data supplied from each sensor/actuator 102, 104 (702). The baseline data is representative of sensor data that was generated when ultrasonic waves were transmitted into the structure 110 with no defects present. It is noted that the baseline data may be stored in memory 124 (see FIG. 1). In the depicted embodiment, the memory 124 is part of the processing and control functions 122 portion of the processor 106, but in other embodiments it may be any one of numerous suitable external memory storage devices.

The calculated SDCs (which may also be referred to herein as damage indices (Dis)) are spatially mapped to detect one or more structural defects in the structure 110 (704). A damage map is generated from the spatially mapped SDCs (706), and image rendering display commands representative of the damage map are at least selectively generated (708). The specific manner in which the processor 106 implements each of these process steps may vary, but in a particular embodiment the process 700 that the processor 106 is configured to implement is referred to herein as WEMAT, which stands for Weighted Spatial Mapping of Signal Difference Coefficients using Triangulation. This process 700, which will be described in more detail momentarily, overcomes the drawbacks of presently known processes because it uses more robust SDC calculations, which mitigates the impact of baseline and actual signal synchronization. The process 700 also uses a different model to spatially map the SDCs, which decreases sensitivity to various parameters and mitigates the impact of non-uniform coverage of the monitored area.

The SDC calculations that processor 106 is configured to implement (702) uses the following equation (1):

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}}, \quad \text{(Eq. 1)}$$

where, $X_{e0k}$ and $X_{ek}$ are the complex envelopes associated with the baseline data and sensor data, respectively, $\mu_{x_{e0}}$ and $\mu_{x_e}$ are mean values of the baseline data and sensor data, respectively, and i and j are indices associated with paths between pairs of the first and second sensor/actuator 102, 104. The complex envelopes associated with the baseline data ($X_{e0k}$) and the sensor data ($X_{ek}$) may be derived using any one of numerous known signal transformation techniques. In one particular embodiment, however, the complex envelopes are derived using the Hilbert Transform. The calculated SDCs identify which paths are affected by the presence of a defect, and are measures of the impact of the defect on the path.

Before proceeding further, it is noted that any one of numerous other SDC metrics may also be used. Some non-limiting examples include correlation index, a mean signal amplitude, and total signal energy metrics. The correlation index is based on a correlation between baseline and actual signal, and a correlation between envelopes of baseline and actual signals. The mean signal amplitude is based on a difference between the mean signal amplitudes of baseline and actual signals, and the mean signal amplitudes of the difference between baseline and actual signals. The total signal energy is based on differences between the total signal energy of baseline and actual signals, and the total signal energy of the differences between baseline and actual signals.

As noted above, the calculated SDCs are spatially mapped to detect one or more structural defects in the structure 110 (704). To implement this functionality, the processor 106, at least in the depicted embodiment, is configured to use a basis function to spatially map the calculated SDCs. The particular basis function used assumes that a defect causes the values of the SDCs to change in direct wave paths, and that the impact on the SDCs decreases with increasing distance of the defect from a direct path. In this regard, the basis function is defined using the following equation (2):

$$B_{wij}(x, y) = B_{ij}(x, y)w_{ij}(x, y), \quad \text{(Eq. 2)}$$

where x and y are spatial coordinates, i and j are indices associated with the first and second sensor/actuators 102, 104, $w_{ij}(x,y)$ is a 2D cosine window, and $B_{ij}(x,y)$ is also basis function that is defined using the following equation (3):

$$B_{ij}(x, y) = \frac{d_{ij}(x, y)}{d_i(x, y) + d_j(x, y)}, \quad \text{(Eq. 3)}$$

where x and y are spatial coordinates, i and j are indices associated with the first and second sensor/actuators 102, 104, $d_{ij}$ is a direct path length between first or second sensor/actuator-i (when configured as an actuator) and second or first sensor/actuator-j (when configured as a sensor), $d_j$ is a distance from a first or second sensor/actuator-i (when configured as an actuator) to a point with coordinates (x,y), $d_j$ is a distance from a second or first sensor/actuator-j (when configured as a sensor) to the point with coordinates (x,y).

Before proceeding further, it is noted that it may be readily apparent, at least to the skilled artisan, that equation (2) is the result of weighting the basis function of equation (3) by means of an appropriate 2D window. Thus, equation (2) may be thought of as a "modified basis function." The modified basis function was defined because the confidence in image values in a resultant damage map image will depend upon the density of direct paths in particular image area. This density is higher in the central areas of the damage map image and decreases with increasing distance from the central areas. The lower direct path density, which typically occurs relatively close to the position of the sensor/actuators 102, 104, can result in false artifacts being generated in the resultant damage map image. The modified basis function mitigates this phenomenon.

Returning once again to the description, the spatially mapped SDCs that are calculated using equation (2) are used to generate a damage map (706). Although a damage map may be generated using any one of numerous known techniques, in one particular embodiment, the processor 106 is configured to generate a damage map using the following equation (4):

$$D(x, y) = \sum_{ij}(1 - SDC_{ij})B_{wij}(x, y), \quad \text{(Eq. 4)}$$

where D(x,y) is a damage index at spatial coordinates (x,y). An example of a damage map that may be generated using equations (2) and (4), and which illustrates examples of each of the variables di, dj, dij, and (x, y), for one particular sensor/actuator-i, sensor/actuator-j pair, is depicted in FIG. 8.

Figure 8:
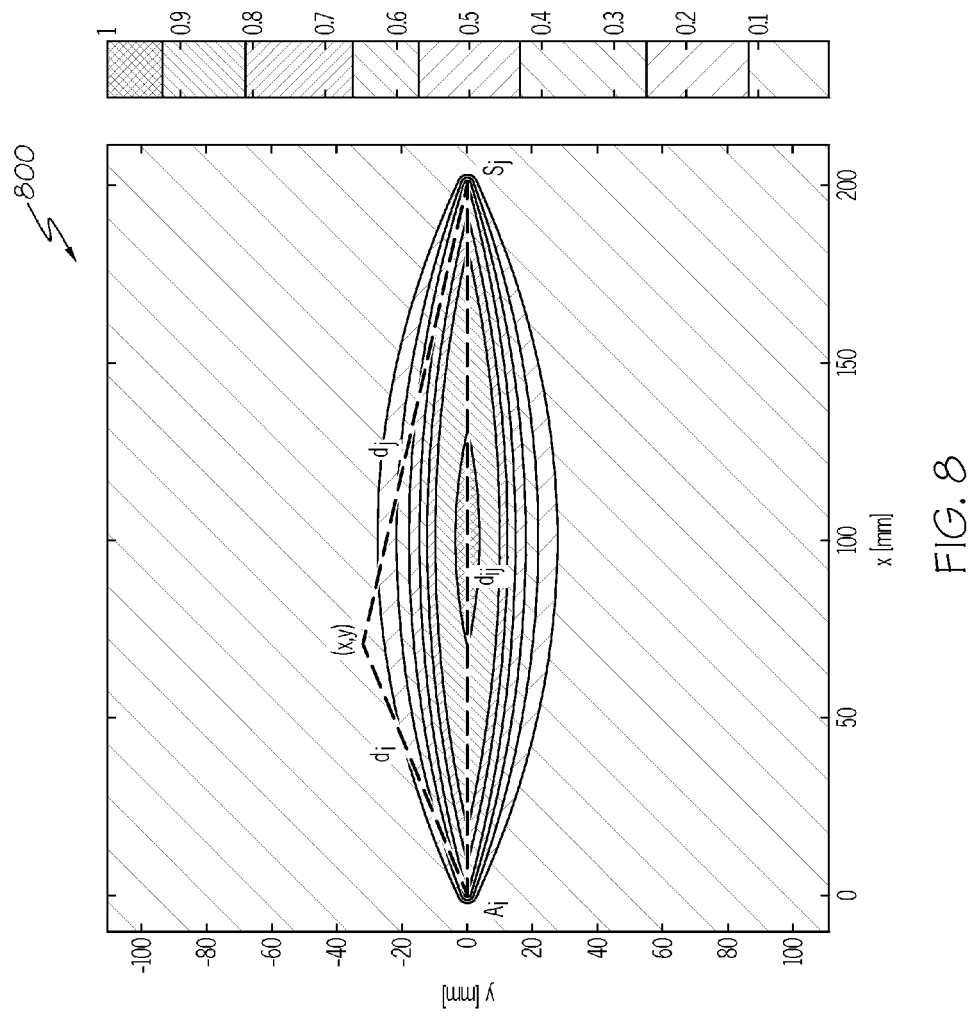
FIG. 8 depicts an image of an exemplary damage map that may be generated by the system of FIG. 1, and rendered on a display device that forms part of the system of FIG. 1.

The exemplary image 800 that is depicted in FIG. 8 may be rendered on the display device 108. To do so, the processor 106 at least selectively generates image rendering display commands representative of the damage map (708) and supplies the image rendering display commands to the display device 108. As FIG. 1 depicts, the display device 108 is coupled to receive the image rendering display commands from the processor 106. The display device 108 is configured, upon receipt of the image rendering display commands, to render images representative of the damage map 800. It will be appreciated that the display device 108 may be implemented using any one of numerous known displays suitable for rendering graphic, iconic, and/or textual data in a format viewable by a user. Some non-limiting examples of such displays include various cathode ray tube (CRT) displays, and various flat panel displays, such as various types of LCD (liquid crystal display), TFT (thin film transistor) displays, and OLED (organic light emitting diode) displays. The display may additionally be based on a panel mounted display, a HUD (head-up display) projection, or any one of numerous other known technologies. It is further noted that the system 100 could be implemented with more than one display device 108, if needed or desired.

The system and method described above provides for the detection, localization, and size evaluation of structural defects in real-time, without relying on the precise positioning of the sensor/actuators, and without relatively complicated, long, voluminous, and heavy sensor wiring. The system and method are additionally relatively insensitive to phase synchronization between the baseline and actual signals, and do not generate images that include false artifacts if certain parameters are not optimally set. However, as will now be described, even more sophisticated signal processing methods have been developed for use in the system 100 of FIG. 1 for both hot-spot monitoring of structural defects and for multi-defect monitoring. Each of these additional signal processing methods will now be described, beginning first with the hot-spot monitoring.

Figure 9:
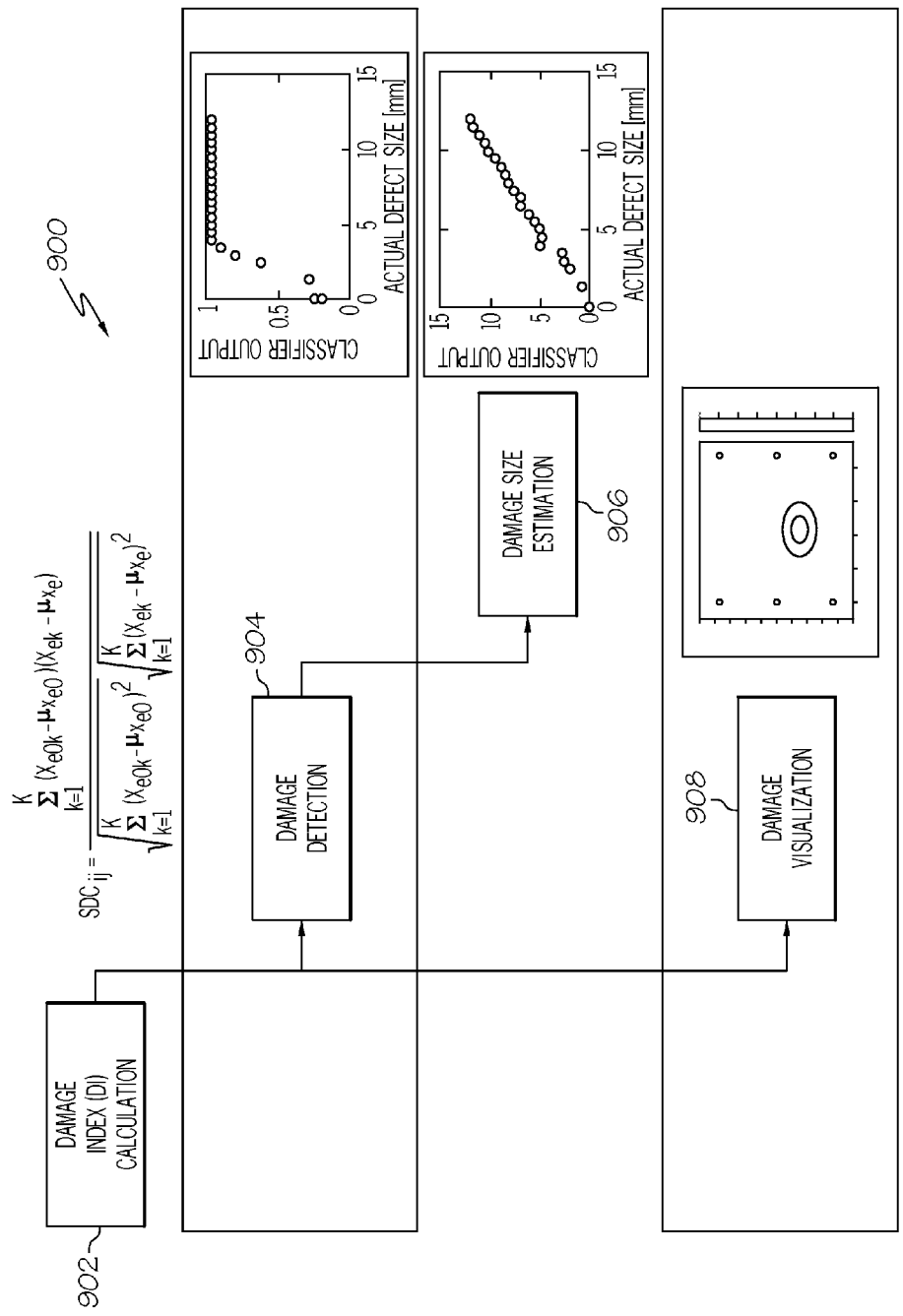
FIG. 9 depicts a schematic representation of a particular process that the system of FIG. 1 may implement for automated hot-spot monitoring.

For hot-spot monitoring, certain assumptions are imposed in order to significantly simplify the automated analysis of the structure state. These assumptions are that the type of the defect is known, only one defect can develop in the monitored area, and the location of the structural defect is known. With these assumptions, the structural health monitoring problem reduces to decision making regarding the presence of the defect and an estimation of the actual size of the defect. A schematic representation of a particular preferred process 900 that the system 100 may implement for hot-spot monitoring is depicted in FIG. 9, and will now be described.

The first step of the process 900 includes calculating DIs/SDCs from baseline data and from the sensor data supplied from each sensor/actuator 102. Any one of the previously described metrics may be used to calculate the DIs/SDCs. The DIs/SDCs are calculated for a defined set of paths, with each path associated with a particular sensor/actuator pair 102. Not all paths need to be included in the processing, so only paths going through the monitored area should be considered.

Figure 10:
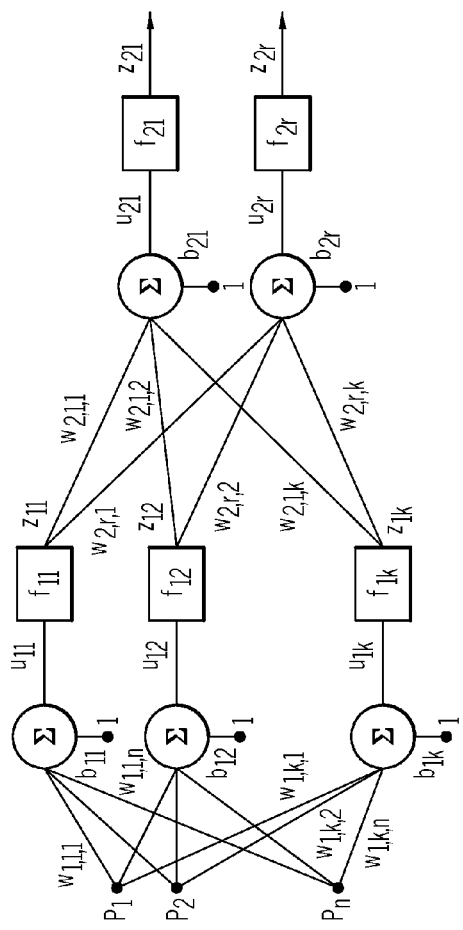
FIGS. 10 and 11 depict different embodiments of artificial neural network topologies.
Figure 11:
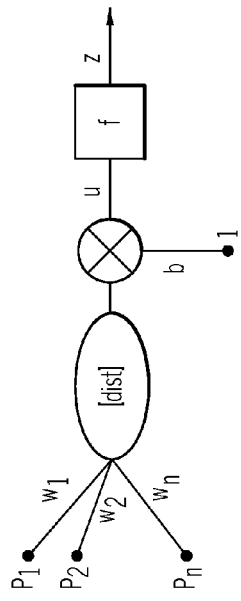

After the SDCs are calculated, the process 900 implements steps to detect the presence/non-presence of a defect (904), and an estimation of the size of a defect that is determined to be present (906). To determine whether a defect is present and, if so, its size, the processor 106 implements artificial neural networks. It will be appreciated that the processor 106 may implement any one of numerous known artificial neural network topologies. In a particular embodiment, a multi-layer feed-forward network topology is used to detect the presence/non-presence of a defect, and a generalized regression neural network topology is used for defect size estimation. For completeness, an exemplary embodiment of a two layer feed forward network 1000 is depicted in FIG. 10, and an exemplary embodiment of a radial basis neuron 1100, which is used to implement a generalized regression neural network topology, is depicted in FIG. 11.

When a defect is determined to be present, the processor also implements a damage visualization step (908). The specific manner in which the processor 106 implements each the damage visualization step may vary, but in a particular embodiment the processor 106 is configured to implement the previously-described WEMAT algorithm. As was described above, with this algorithm a damage map is generated from the DIs/SDCs, and image rendering display commands representative of the damage map are at least selectively generated.

Figure 12:
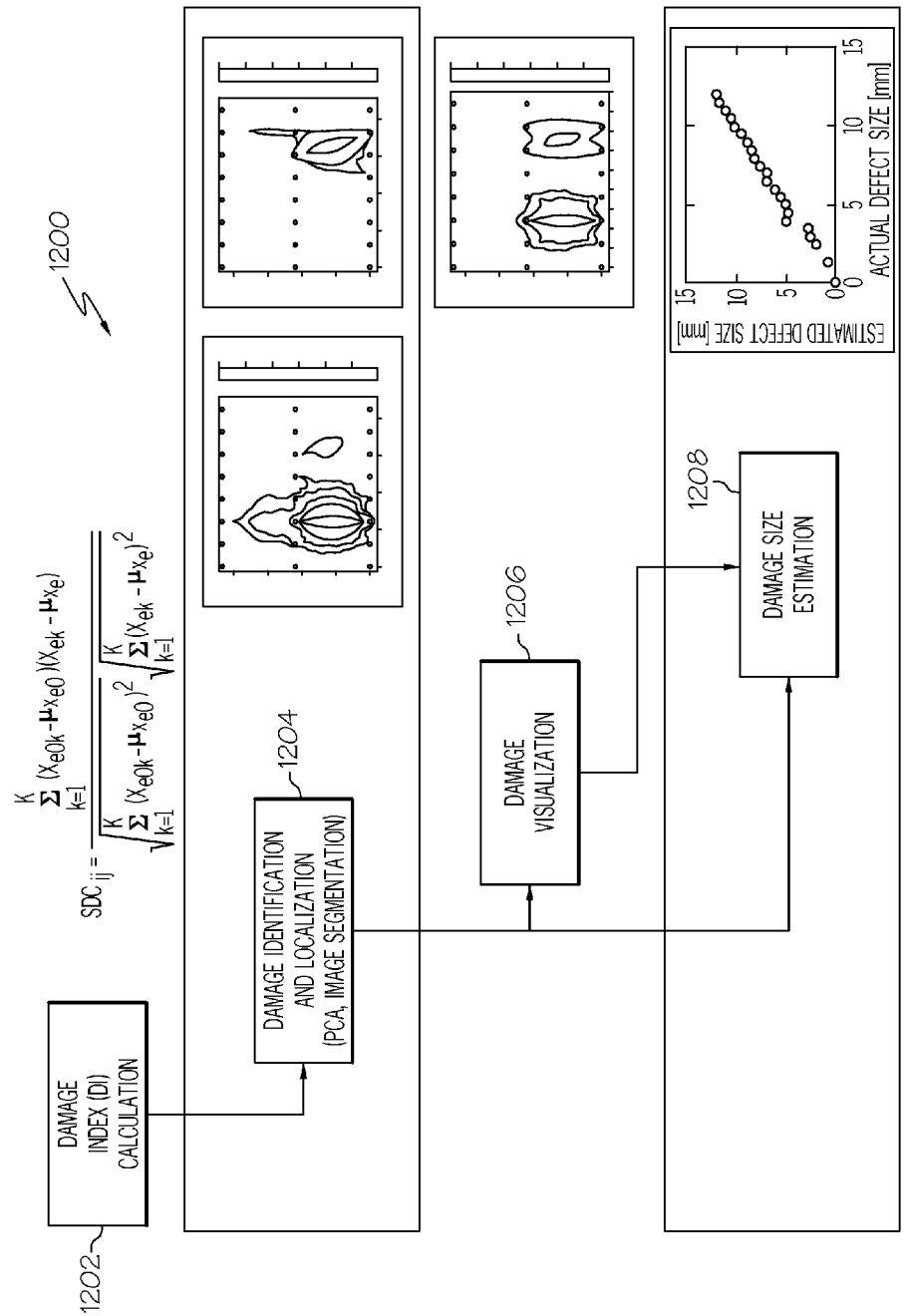
FIG. 12 depicts a schematic representation of a particular process that the system of FIG. 1 may implement for automated multi-defect monitoring.

Referring now to FIG. 12, a schematic representation of a particular preferred process 1200 for use in the system 100 of FIG. 1 to implement automated multi-defect monitoring is depicted. As before, the first step (1202) of the process 1200 is the calculation of the DIs/SDCs from baseline data and from the sensor data supplied from each sensor/actuator 102. Any one of the previously described metrics may be used to calculate the DIs/SDCs.

Because multi-site damage may occur when this process is being implemented, the next step that the processor 106 implements is identifying and localizing the individual defects (1204). Thereafter, the defect is visualized (1206), using the previously described WEMAT algorithm, and then defect size is estimated (1208). The particular manner in which individual defects are identified and localized may vary, but in the depicted embodiment this step (1204) is based on Principal Component Analysis (PCA) and image segmentation. The PCA uses current data, as well as data from a number of previous measurements, as the input matrix. As may be appreciated, a time window of appropriate length is preferably applied in order to limit the size of the input matrix. The matrix, which is subjected to PCA, is composed of sets of DI/SDC vectors for the number of consecutive measurements. Relations between individual DI/SDC vectors, and their significance, are represented using PCA eigenvectors. Each significant PCA eigenvector is related to one defect, and the number of significant eigenvectors is controlled using an appropriate threshold value. An embodiment of the PCA 1300 and image segmentation processes 1320 that are used is depicted in FIG. 13, and with reference thereto will now be described.

Figure 13:
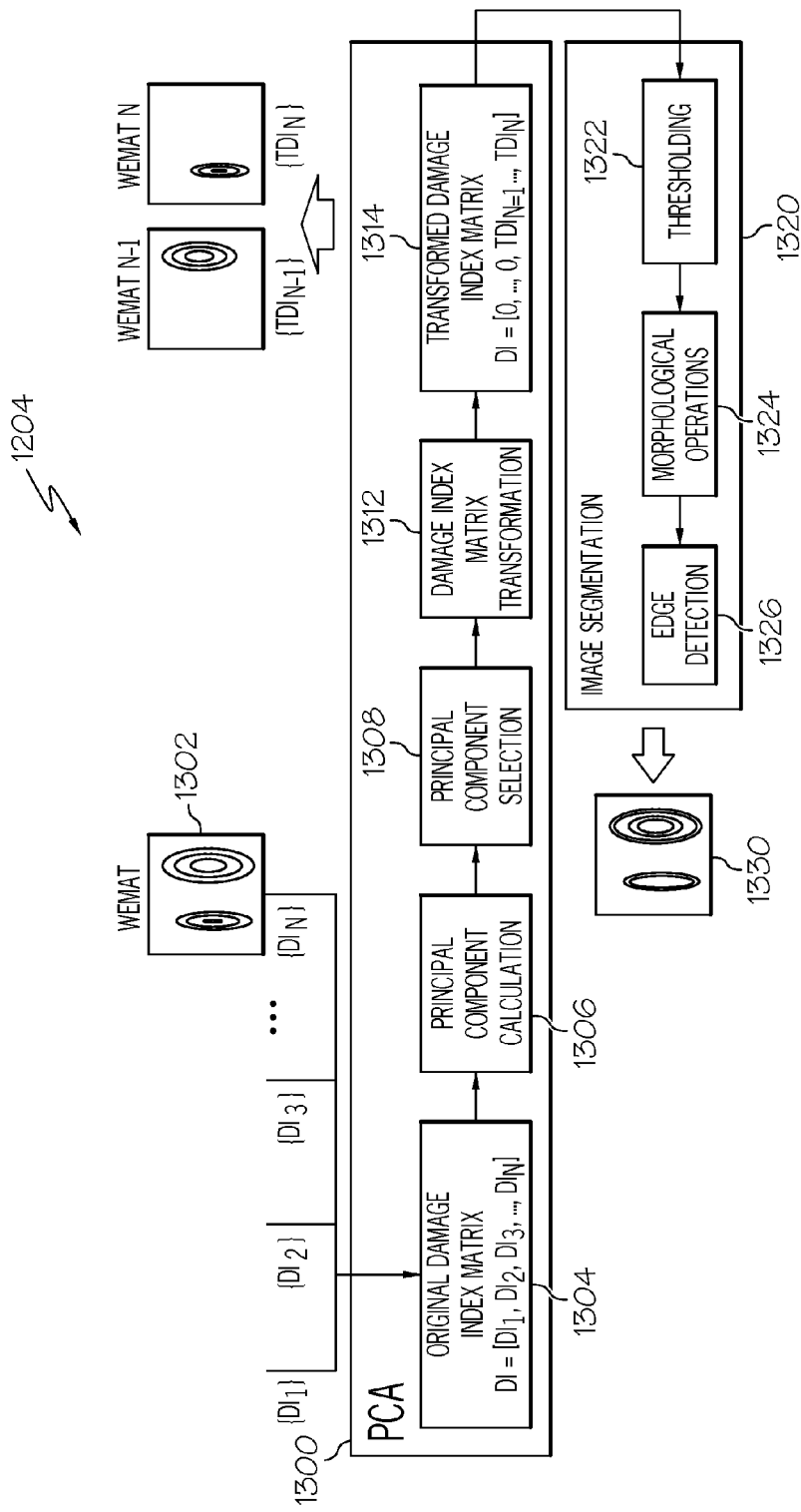
FIG. 13 depicts a schematic representation of a particular principle component analysis (PCA) and image segmentation processes that the system of FIG. 1 may implement.

As FIG. 13 depicts, the current DI/SDC vector (e.g., $DI_N$), and the previous (N-1) DI/SDC vectors (e.g., $DI_{N-1}$, $DI_{N-2}$, ..., $DI_1$) are used as the inputs to the algorithm. Moreover, the current DI/SDC vector (e.g., $DI_N$) is processed using the WEMAT algorithm to generate a WEMAT image 1302 showing the current state of the monitored area. More specifically, the inputs are organized into an input matrix, such as the one depicted in FIG. 14, where $DI_{ij}$ is a $j^{-th}$ damage index pertaining to an $i^{-th}$ DI vector, i.e. to the $i^{-th}$ measurement, and which is referred to herein as the original damage index matrix 1304.

The original damage index matrix 1304 is then subjected to various principle component calculations 1306 to identify the most significant principle components. These calculations include, for example, subtracting the mean value from each DI/SDC vector in the matrix, using the following equation:

$$DI_{ij} = DI_{ij} - \text{mean}(DI_i).$$

A covariance matrix is then calculated, followed by a calculation of the covariance matrix eigenvectors and eigenvalues. The following equation provides an example of how the covariance between two vectors X and Y may be calculated:

$$\text{cov}(X, Y) = \frac{\sum_{i=1}^{N}(X_i - \overline{X})(Y_i - \overline{Y})}{(N-1)},$$

where N is number of vector components. It is noted that the number of different covariance values for an N-dimensional data set is:

$$n_{cov} = \frac{n!}{2(n-2)!},$$

where n corresponds to a number of vectors considered for the covariance matrix calculation.

The basic formula for calculating covariance matrix eigenvectors and eigenvalues calculation is:

$$C^{n \times n} x = \lambda x,$$

where $C^{n \times n}$ is the covariance matrix, x is the eigenvector, and $\lambda$ is the corresponding vector of eigenvalues.

After the principle component calculations 1306, a principle component selection process 1308 is implemented. Each calculated eigenvector has one particular eigenvalue representing the eigenvector's significance. Thus, the eigenvectors are arranged according to their eigenvalues size, and the eigenvectors with eigenvalues greater than a threshold are selected. Each selected eigenvector corresponds to one change of the monitored structure state, e.g. emergence of a new defect in the series of measurements, and size of the eigenvalue represents its significance.

In order to provide original data solely in terms of the selected eigenvectors, a damage index matrix transformation 1312 is implemented using the following transformation:

$$TDI = EV \times DI^T,$$

where TDI is the transformed matrix of the DIs/SDCs, EV is the matrix with eigenvectors in rows with the most significant eigenvector on the top, and $DI^T$ is mean-adjusted matrix of DIs/SDCs transposed, i.e. DIs/SDCs for one particular measurement are in rows.

Now, to transform the data back to the original coordinate system, and thereby generate a transformed damage index matrix 1314, the following transform is used:

$$ODI = EV^T \times TDI + OM,$$

where ODI is the transformed data expressed in terms of the original coordinate system, EV is a transposed matrix of the selected eigenvectors, TDI is the transformed matrix of the DIs/SDCs, and OM is a matrix of the mean of the original data.

Each non-zero DI vector (ODI) corresponds to a potential defect. A WEMAT image (e.g., $WEMAT_N$, $WEMAT_{N-1}$, ... $WEMAT_1$) is calculated for each of non-zero DI vector (ODI), and each WEMAT image is processed using image processing algorithms implemented in the image segmentation process 1320. The image segmentation process 1320 involves three major image processing algorithms, thresholding 1322, morphological operations 1324, and edge detection 1326, each of which will now be described.

The goal of thresholding 1302 is to segment an image into regions of interest and to remove all other regions. Numerous and varied image thresholding algorithms may be used, but in a particular embodiment a thresholding algorithm that isolates objects of interest having values different from the image background is used. With this algorithm, a value of either 1 or 0 is assigned to each pixel, depending on whether the pixel belongs to an object of interest or to the background. Although it may vary, the thresholding process is expressed as follows:

$$b(m, n) = \begin{cases} 0 & a(m, n) \leq k \\ 1 & \text{otherwise} \end{cases}$$

where a(m,n) is the original image, b(m,n) is the image after thresholding, and k is a predetermined threshold value that is specified as a fractional part of a maximal image value (e.g., 50% or 75%).

The morphological operations 1324 are used to enhance the thresholded image before applying edge detection 1326. The morphological operation 1326 processes objects in the input image based on the characteristics of its shape, which are encoded in a structuring element. The structuring element is a set of points (often represented as a binary image) that has its origin at the center pixel, and it is normally much smaller than the input image. The structuring element is shifted over the image and at each position of the center of the structuring element the original image pixels are compared with the structuring element pixels and the center pixel in the original image is set to determined value according to particular set operator. Thus, the structuring element and the particular set operator define a morphological operator.

Dilation and erosion are the two fundamental morphological operators, and are defined, as follows, by Minkowski addition and Minkowski subtraction:

$$D(A, B) = A \oplus B = \bigcup_{\beta \in B} (A + \beta)$$

$$E(A, B) = A \otimes (-B) = \bigcap_{\beta \in B} (A - \beta)$$

where A is the original image and B is structuring element. Dilation, in general, causes objects to grow in size, and erosion causes objects to shrink. The amount and the manner in which the objects grow or shrink depend upon the structuring element.

These two operators can be applied in different combinations in order to obtain more sophisticated operations such as, for example, opening and closing. Opening of an image is given by first eroding the image with a structuring element and then dilating the result using the same structuring element, as follows:

$$O(A, B) = A \circ B = D(E(A, B), B),$$

and closing of an image is defined by first dilating the image with a structuring element and then eroding the result using the same structuring element, as follows:

$$E(A, B) = A \bullet B = E(A, -B), -B).$$

Opening an image with an appropriate structuring element will smooth image contours, break narrow isthmuses, and eliminate small islands. Closing an image with an appropriate structuring element will smooth contours, fuse narrow breaks and long thin gulfs, eliminate small holes, and fill gaps in contours. Thus, a combination of openings and closings can be used to remove small holes and small speckles or islands in a binary image. The main objectives of the morphological operation 1326 are to remove "salt and pepper noise" from the image, and to smooth contours of objects to facilitate subsequent edge detection 1326.

As is generally known, an edge is a set of image pixels or contours at which a considerable change in brightness value occurs. Generally, it is difficult to specify a priori which edges correspond to relevant boundaries in an image. Image operations used for edge detection are usually dependent on the particular application. Here, binary images are being processed, so a binary perimeter edge detection process may be used. Alternatively, a more sophisticated method, which uses gradient operators, may be implemented.

After the image segmentation process 1320, the defects are localized 1330. Defect localization 1330 is implemented using position information of the individual image segments that are supplied by the image segmentation process 1320. More specifically, at least in a particular embodiment, the position of a defect corresponds to the center of the image segment. There are several alternative techniques that may be used to define the center of an image segment. Some non-limiting examples include the geometrical center, the arithmetical center, and the maximal image value, which are defined below, in the order just listed:

$$(x_0, y_0) = \frac{1}{N} \sum_{i \in I} (x_i, y_i),$$

$$(x_0, y_0) = \frac{\sum_{i \in I} v_i (x_i, y_i)}{\sum_{i \in I} v_i},$$

$$(x_0, y_0) = (x_i, y_i) \mid v_i = \max(v) \wedge i \in I,$$

where, in each instance, $x_0$ and $y_0$ are coordinates of the image segment center (location of the defect), $x_i$ and $y_i$ are image coordinates, N is number of image pixels in the image segment, I is set of the image pixels defined by the image segment, and $v_i$ is the image value for particular image pixel $(x_i, y_i)$. It will be appreciated that any one of numerous other algorithms useful for the calculation of the image segment may be used. Selection of the algorithm may depend, for example, on the particular application and defect type.

No matter the specific algorithms used, each of the image segments that are identified and localized (1204) is described by means of a feature vector. The feature vector consists of a set of statistical parameters, which are calculated from the image area bounded by the segment borders. The particular composition of the feature vector may vary, and may depend on the application, and those parameters that have a strong correlation with defect size should be considered as the most suitable. In some embodiments, the feature vector may include one or more of the length of the image segment border, the area enclosed by the segment border, the sum of the image values, the maximal image value, the mean image value, the image median, and various parameters derived from the image histogram or from a probability distribution function characterizing a distribution of the image values. The feature vectors are used to estimate defect size (1208).

To estimate defect size (1208), the processor 106 implements a transformation function (f) that maps the feature vectors from feature vector space to the space of damage sizes as follows. The transformation is defined as follows:

$$a = f(\overline{P}),$$

where a is defect size, and $\overline{P}$ is the feature vector defines as follows:

$$\overline{P} = [p_1, p_2, \ldots, p_n],$$

where $p_1, p_2, \ldots, p_n$ are individual parameters defined on the area defined for particular image segment.

It will be appreciated that the transformation function can be realized by means of linear regression or by means of a method of artificial intelligence, e.g. artificial neural networks.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The word "exemplary" is used exclusively herein to mean "serving as an example, instance, or illustration." Any embodiment described herein as "exemplary" is not necessarily to be construed as preferred or advantageous over other embodiments.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal In the alternative, the processor and the storage medium may reside as discrete components in a user terminal In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for detecting and evaluating structural defects, comprising the steps of:
    storing baseline data associated with a structure, the baseline data representative of sensed ultrasonic waves that were transmitting into the structure with no defects;
    transmitting ultrasonic waves into the structure from a plurality of actuators that are coupled to the structure;
    sensing, with a plurality of sensors that are coupled to the structure and spaced apart from the actuators, the ultrasonic waves transmitted into the structure from the plurality of actuators, to thereby generate and supply sensor data;
    calculating signal difference coefficients from the baseline data and the sensor data; and
    spatially mapping the calculated signal difference coefficients to detect one or more structural defects in the structure,
    wherein the signal difference coefficients (SDCs) are calculated using the following equation:

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}},$$

wherein:
    $X_{e0k}$, $X_{ek}$ are envelopes associated with the baseline data and sensor data, respectively,
    $\mu_{x_{e0}}$, $\mu_{x_e}$ are mean values of the baseline data and sensor data, respectively, and
    i and j are indices associated with a particular actuator and sensor, respectively.

2. The method of claim 1, further comprising generating a damage map from the spatially mapped signal difference coefficients.

3. The method of claim 2, further comprising rendering an image representative of the damage map.

4. The method of claim 1, wherein the SDCs are spatially mapped using a basis function, which is defined using the following equation:

$$B_{wij}(x, y) = B_{ij}(x, y)w_{ij}(x, y),$$

wherein:

$$B_{ij}(x, y) = \frac{d_{ij}(x, y)}{d_i(x, y) + d_j(x, y)},$$

x, y are spatial coordinates,
i, j are indices of actuator and sensor,
$d_{ij}$ is a direct path length between actuator-i and sensor-j,
$d_i$ is a distance from the actuator-i to a point with coordinates (x,y),
$d_j$ is a distance from sensor-j to the point with coordinates (x,y), and
$w_{ij}(x,y)$ is a 2D cosine window.

5. The method of claim 4, further comprising generating a damage map using the following equation:

$$D(x, y) = \sum_{ij}(1 - SDC_{ij})B_{wij}(x, y),$$

wherein D(x,y) is a damage index at spatial coordinates (x,y).

6. The method of claim 5, further comprising rendering an image representative of the damage map.

7. The method of claim 1, wherein:
    each of the plurality of actuators is configured to selectively act as a sensor;
    each of the plurality of sensors is configured to selectively act as an actuator, and
    the method further comprises:
        selectively configuring each sensor to act as an actuator and transmitting ultrasonic waves therefrom,
        selectively configuring each actuator to act as a sensor and sensing the ultrasonic waves therewith.

8. The method of claim 1, further comprising:
    mounting each actuator on a first flexible printed circuit;
    mounting each sensor on a second flexible printed circuit.

9. The method of claim 8, further comprising coupling the first and second printed circuits to the structure.

10. A structural defect detection and evaluation system, comprising:
    a plurality of first sensor/actuators adapted to be coupled to a structure, each first sensor/actuator configured to selectively transmit ultrasonic waves into the structure;
    a plurality of second sensor/actuators adapted to be coupled to the structure and, when coupled thereto, to be spaced apart from each of the first sensor/actuators, each second sensor/actuator configured to selectively sense the ultrasonic waves transmitted from one or more of the first sensor/actuators and generate sensor data; and
    a processor coupled to receive the sensor data and configured, upon receipt thereof, to:
        calculate signal difference coefficients from the sensor data and baseline data, the baseline data representative of sensed ultrasonic waves that were transmitting into the structure with no defect present, and
        spatially map the calculated signal difference coefficients to detect one or more structural defects in the structure, wherein the processor is configured to calculate the signal difference coefficients (SDCs) using the following equation:

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}},$$

wherein:
$X_{e0k}$, $X_{ek}$ are envelopes associated with the baseline data and sensor data,
$\mu_{x_{e0}}$, $\mu_{x_e}$ are mean values of the baseline data and sensor data, and
i and j are indices associated with a particular actuator and sensor.

11. The system of claim 10, wherein the processor is further configured to generate a damage map from the spatially mapped signal difference coefficients.

12. The system of claim 11, further comprising
a display device coupled to receive image rendering display commands from the processor and configured, upon receipt thereof, to selectively render images representative of the image rendering display commands,
wherein the processor is further configured to selectively generate image rendering display commands representative of the damage map.

13. The system of claim 10, wherein the processor is configured to spatially map the SDCs using a basis function, which is defined using the following equation:

$$B_{wij}(x, y) = B_{ij}(x, y)w_{ij}(x, y),$$

wherein:

$$B_{ij}(x, y) = \frac{d_{ij}(x, y)}{d_i(x, y) + d_j(x, y)},$$

x, y are spatial coordinates,
i, j are indices of actuator and sensor,
$d_{ij}$ is a direct path length between actuator-i and sensor-j,
$d_j$ is a distance from the actuator-i to a point with coordinates (x,y),
$d_j$ is a distance from sensor-j to the point with coordinates (x,y), and
$w_{ij}(x,y)$ is a 2D cosine window.

14. The system of claim 13, wherein the processor is further configured to generate a damage map using the following equation:

$$D(x, y) = \sum_{ij}(1 - SDC_{ij})B_{wij}(x, y),$$

wherein D(x,y) is a damage index at spatial coordinates (x,y).

15. The system of claim 14, further comprising:
a display device coupled to receive image rendering display commands from the processor and configured, upon receipt thereof, to selectively render images representative of the image rendering display commands,
wherein the processor is further configured to selectively generate image rendering display commands representative of the damage map.

16. The system of claim 10, wherein:
each second sensor/actuator is further configured to selectively to transmit ultrasonic waves; and
each first sensor/actuator is further configured to selectively sense transmitted ultrasonic waves.

17. The system of claim 10, wherein:
each first sensor/actuator is mounted on a first flexible printed circuit; and
each second sensor/actuator is mounted on a second flexible printed circuit.

18. A structural defect detection and evaluation system, comprising:
a plurality of first sensor/actuators, each of the first sensor/actuators mounted on a first flexible printed circuit and adapted to be coupled to a structure, each first sensor/actuator configured to selectively transmit ultrasonic waves into the structure;
a plurality of second sensor/actuators, each of the second sensor/actuators mounted on a second flexible printed circuit and adapted to be coupled to the structure, each second sensor/actuator, when coupled to the structure, spaced apart from each of the first sensor/actuators, each second sensor/actuator configured to selectively sense the ultrasonic waves transmitted from one or more of the first sensor/actuators and generate sensor data;
a display device coupled to receive image rendering display commands and configured, upon receipt thereof, to selectively render images representative of the image rendering display commands; and
a processor coupled to receive the sensor data and configured, upon receipt thereof, to:
calculate signal difference coefficients from the sensor data and baseline data, the baseline data representative of sensed ultrasonic waves that were transmitting into the structure with no defect present,
spatially map the calculated signal difference coefficients to detect one or more structural defects in the structure,
to generate a damage map from the spatially mapped signal difference coefficients, and
selectively generate image rendering display commands representative of the damage map,
wherein the processor is configured to calculate the signal difference coefficients (SDCs) using the following equation:

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}},$$

wherein:
$X_{e0k}$, $X_{ek}$ are envelopes associated with the baseline data and sensor data,
$\mu_{x_{e0}}$, $\mu_{x_e}$ are mean values of the baseline data and sensor data, and
i and j are indices associated with a particular actuator and sensor.

19. A method for detecting and evaluating structural defects, comprising the steps of:

storing baseline data associated with a structure, the baseline data representative of sensed ultrasonic waves that were transmitting into the structure with no defects;

transmitting ultrasonic waves into the structure from a plurality of actuators that are coupled to the structure;

sensing, with a plurality of sensors that are coupled to the structure and spaced apart from the actuators, the ultrasonic waves transmitted into the structure from the plurality of actuators, to thereby generate and supply sensor data;

calculating signal difference coefficients from the baseline data and the sensor data;

supplying the signal difference coefficients to a trained neural network to detect whether a defect is present; and using the trained artificial neural network to estimate a size of a defect that is determined to be present, wherein the signal difference coefficients (SDCs) are calculated using the following equation:

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}},$$

wherein:
$X_{e0k}$, $X_{ek}$ are envelopes associated with the baseline data and sensor data, respectively,
$\mu_{x_{e0}}$, $\mu_{x_e}$ are mean values of the baseline data and sensor data, respectively, and
i and j are indices associated with a particular actuator and sensor, respectively.

20. The method of claim 19, further comprising:
spatially mapping the calculated signal difference coefficients to detect one or more structural defects in the structure generating; and
generating a damage map from the spatially mapped signal difference coefficients.

21. A method for detecting and evaluating structural defects, comprising the steps of:
storing baseline data associated with a structure, the baseline data representative of sensed ultrasonic waves that were transmitting into the structure with no defects;

transmitting ultrasonic waves into the structure from a plurality of actuators that are coupled to the structure;

sensing, with a plurality of sensors that are coupled to the structure and spaced apart from the actuators, the ultrasonic waves transmitted into the structure from the plurality of actuators, to thereby generate and supply sensor data;

calculating signal difference coefficients from the baseline data and the sensor data;

spatially mapping the calculated signal difference coefficients to detect one or more structural defects in the structure generating;

a damage map from the spatially mapped signal difference coefficients;

identifying and localizing the individual defects using Principal Component Analysis (PCA) and image segmentation; and estimating defect size, wherein the signal difference coefficients (SDCs) are calculated using the following equation:

$$SDC_{ij} = \frac{\sum_{k=1}^{K}(X_{e0k} - \mu_{x_{e0}})(X_{ek} - \mu_{x_e})}{\sqrt{\sum_{k=1}^{K}(X_{e0k} - \mu_{x_{e0}})^2}\sqrt{\sum_{k=1}^{K}(X_{ek} - \mu_{x_e})^2}},$$

wherein:
$X_{e0k}$, $X_{ek}$ are envelopes associated with the baseline data and sensor data, respectively,
$\mu_{x_{e0}}$, $\mu_{x_e}$ are mean values of the baseline data and sensor data, respectively, and
i and j are indices associated with a particular actuator and sensor, respectively.

* * * * *